United States Patent [19]
Emura et al.

[11] Patent Number: 5,856,590
[45] Date of Patent: Jan. 5, 1999

[54] PROCESS FOR PRODUCING CIS-4-T-BUTYLCYCLOHEXANOL

[75] Inventors: Makoto Emura; Takaaki Toyoda; Nobuo Seido, all of Kanagawa; Ryoji Noyori, Aichi; Takao Ikariya, Aichi; Takeshi Ohkuma, Aichi, all of Japan

[73] Assignee: Takasago International Corporation, Tokyo, Japan

[21] Appl. No.: 812,540

[22] Filed: Mar. 7, 1997

[30]     Foreign Application Priority Data

Mar. 7, 1996  [JP]  Japan .................................. 8-050310

[51] Int. Cl.$^6$ ................................................. C07C 29/145
[52] U.S. Cl. ........................... 568/835; 568/832; 568/834
[58] Field of Search .................... 568/822, 832, 568/834, 835

[56]     References Cited

U.S. PATENT DOCUMENTS

| | | |
|---|---|---|
| 4,343,955 | 8/1982 | Ohsima . |
| 4,916,252 | 4/1990 | Sayo . |
| 5,107,038 | 4/1992 | Weinstein ................... 568/834 |
| 5,160,498 | 11/1992 | Weinstein ................... 568/834 |

FOREIGN PATENT DOCUMENTS 764769  of 0000  Japan .

OTHER PUBLICATIONS

J Org Chem "Stereoselective Hydrogenation of Simple Ketones Catalyzed by Ruthenium (II) Complexes", Ohkuma, 61 pp. 4872–4873, Aug. 1996.

Shigeo Nishimura et al., *Chemistry Letters,* pp. 963–966 (1977).

E.L. Ernest et al., *Organic Synthesis,* vol. 50, pp. 13–15 (1970).

*Beilstein Handbook of Organic Chemistry,* E III 6, p. 126 (1960).

S. Arctander, *Perfume and Flavor Chemicals,* Montclair, N.J. (1969), monograph No. 441.

H.C. Brown et al., *J. Am. Chem. Soc.,* vol. 98, pp. 3383–3384 (1979).

T. Ohkuma et al., *J. Am. Chem. Soc.,* vol. 117, pp. 10417–10418 (1995).

*Primary Examiner*—Gary Geist
*Assistant Examiner*—Jean F. Vollano
*Attorney, Agent, or Firm*—Sughrue, Mion, Zinn, Macpeak & Seas, PLLC

[57]     ABSTRACT

A process whereby 4-t-butylcyclohexanol with a high content of the cis-isomer, which is useful as a perfume ingredient, can be economically produced on an industrially available scale at a low cost. The process comprises hydrogenating 4-t-butylcyclohexanone by using a specific ruthenium-phosphine complex as a catalyst in the presence of a base containing an alkali metal and an alkylenediamine having from 1 to 6 carbon atoms.

1 Claim, No Drawings

PROCESS FOR PRODUCING CIS-4-T-BUTYLCYCLOHEXANOL

FIELD OF THE INVENTION

This invention relates to a process for producing cis-4-t-butylcyclohexanol having a specific conformation which is particularly useful as a material in the synthesis of perfume ingredients.

BACKGROUND OF THE INVENTION 4-t-Butylcyclohexanol esters, in particular, 4-t-butylcyclohexyl acetate, are publicly known perfume ingredients.

4-t-Butylcyclohexyl acetate has cis- and trans-stereoisomers with respect to the t-butyl and acetoxy groups bonded to the cyclohexane ring. Many of products marketed today are in the form of mixtures of these isomers containing about 30 to 70% by weight of the cis-isomer. However, it is known that these cis- and trans-isomers largely differ from each other in their fragrance qualities and the cis-isomer is preferable to the trans-isomer [S. Arctander, *Perfume and Flavor Chemicals*, Montclair, N.J. (1969), monograph No. 441]. Accordingly, 4-t-butylcyclohexyl acetate with an elevated content of the cis-isomer has been required in the perfume industry.

4-t-Butylcyclohexyl acetate is obtained by acetylation of 4-t-butylcyclohexanol. The conventional method for producing this 4-t-butylcyclohexanol employed as the starting material comprises, for example, hydrogenating 4-t-butylphenol at 160° C. by using Raney nickel as a catalyst [*Beilstein Handbook of Organic Chemistry*, E III 6, p. 126 (1960)). However, the 4-t-butylcyclohexanol obtained by this method contains the cis-isomer only in a small amount of about 20 to 30% by weight. Therefore, the 4-t-butylcylohexyl acetate obtained by acetylating this product contains only about 20 to 30% by weight of the cis-isomer, which makes it undesirable as a perfume ingredient.

Accordingly, there have been proposed several methods for producing 4-t-butylcyclohexanol containing a large amount of the cis-isomer by stereoselectively hydrogenating 4-t-butylcyclohexanone with the use of various metal catalysts, as will be shown hereinbelow.

(a) A method wherein 4-t-butylcyclohexanone is hydrogenated by using an iridium-phosphinic acid complex in isopropanol [E. L. Ernest et al., *Organic Synthesis*, vol. 50, pp. 13–15 (1970)].

(b) A method wherein 4-t-butylcyclohexanone is hydrogenated by using a rhodium catalyst in the presence of conc. hydrochloric acid in isopropanol or tetrahydrofuran [Shigeo Nishimura et al., *Chemistry Letters*, pp. 963–966 (1977)].

(c) A method wherein 4-t-butylcyclohexanone is hydrogenated by using a catalyst system composed of a combination of rhodium with tetrahydroborate, etc., on a specific carrier (JP-B-7-64769; the term "JP-B" as used herein means an "examined Japanese patent publication").

In addition, there has been proposed a method wherein 4-t-butylcyclohexanone is hydrogenated by using lithium trisamylborohydride without using any catalytic reaction [H. C. Brown et al., *J. Am. Chem. Soc.*, vol. 98, pp. 3383–3384 (1979)].

By using these methods, 4-t-butylcyclohexanol containing the cis-isomer at a high ratio of 80% by weight or above can be obtained. To perform on the industrial scale, however, each of these methods suffers from economical problems. Namely, an expensive catalyst should be used in a large amount in each method. In the method (c), for example, a catalyst containing rhodium, which is a very expensive material, should be used at a molar ratio to the starting 4-t-butylcyclohexanone (i.e., the substrate) of $\frac{1}{20}$ or more [molar ratio of substrate/catalyst ≦20]. In the method (a), it is necessary to employ trimethyl phosphite having an intensely offensive odor and a strong acid in large amounts, which elevates the costs of the equipments for ventilation and drainage.

As discussed above, there has been established no industrially available process for producing 4-t-butylcyclohexanol with a large cis-isomer content. Under the existing circumstances, therefore, 4-t-butylcyclohexyl acetate products in the form of mixtures of the cis-isomer with the trans-isomer at a weight ratio of about 30 to 70, which are less expensive but inferior in the value as a perfume, are still manufactured and sold on a large scale, though there are marketed only in a small amount expensive 4-t-butylcyclohexyl acetate products rich in the cis-isomer.

Accordingly, an object of the present invention is to provide a process for economically producing 4-t-butylcyclohexanol having a large content of the cis-isomer, which is highly valuable as a perfume ingredient, at a low cost on an industrially available scale.

Under these circumstances, the present inventors have conducted extensive studies to achieve the above-mentioned object. As a result, they have successfully found that cis-4-t-butylcyclohexanol having a high purity can be obtained by stereoselectively hydrogenating 4-t-butylcyclohexanone by using a catalyst containing inexpensive ruthenium in the presence of a base having an alkali metal or an alkaline earth metal and an amine, thus completing the present invention.

SUMMARY OF THE INVENTION

Accordingly, the present invention provides a process for producing cis-4-t-butylcyclohexanol containing at least 95% by weight of the cis-isomer represented by the following formula (II):

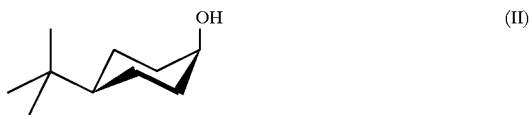

which comprises hydrogenating 4-t-butylcyclohexanone represented by the following formula (I):

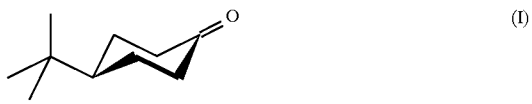

by using as a catalyst a ruthenium-phosphine complex represented by the following formula (III):

wherein $X^1$ represents a halogen atom or a group represented by "$R^1COO$", wherein $R^1$ represents a hydrogen atom, an alkyl group having from 1 to 4 carbon atoms or a halogenated alkyl group having from 1 to 4 carbon atoms; L represents an organic phosphine compound; a and b are each an integer of from 0 to 2, provided that (a+b) is 2; when L is monodentate ligand, c is an integer of from 3 to 4; and when L is bidentate ligand, c is an integer of from 1 to 2;

in the presence of a base having an alkali metal and an alkylenediamine having from 1 to 6 carbon atoms.

DETAILED DESCRIPTION OF THE INVENTION

The ruthenium-phosphine complex to be used as the catalyst in the present invention is a compound having an organic phosphine compound coordinated with ruthenium. It may further have an auxiliary ligand. It may be either a mononuclear complex or a multinuclear complex. As this complex, a commercially available one may be used as such. Alternatively, use can be made therefor of a complex prepared in situ in accordance with a publicly known method. In the latter case, for example, a ligand is added in an amount of 1 to 4 equivalents to ruthenium, to a commercially available ruthenium salt or ruthenium complex. Alternatively, a ruthenium salt or a ruthenium complex and a ligand are separately added in the step of the hydrogenation reaction of the present invention so as to form a complex in the reaction system. It is also possible to use a ligand in excess, a complex mixed with an additive such as triethylamine or a Lewis acid, or a complex which has been activated by reducing.

The organic phosphine compound to be coordinated with ruthenium may be either a monodentate ligand or a multidentate (i.e., bidentate or higher) one. Examples thereof include a monodentate ligand represented by the following formula (IV):

$$PR^2R^3R^4 \qquad (IV)$$

wherein $R^2$, $R^3$ and $R^4$ may be the same or different and each represents an optionally substituted alkyl group, an optionally substituted aralkyl group or an optionally substituted aryl group; or a bidentate ligand represented by the following formula (V):

$$R^5R^6P—A^1—PR^7R^8 \qquad (V)$$

wherein $R^5$, $R^6$, $R^7$ and $R^8$ may be the same or different and each represents an optionally substituted alkyl group, an optionally substituted aralkyl group or an optionally substituted aryl group; and $A^1$ represents an optionally substituted alkylene group, —$A^2$—Ar—Ar—$A^2$— or —Ar—Ar—, wherein $A^2$ represents an optionally substituted alkylene group, and —Ar—Ar— represents a 1,1'-biphenyl group having a binding arm at the 2,2'-position, a 1,1'-binaphthyl group having a binding arm at the 2,2'-position, or a 5,5',6,6',7,7',8,8'-octahydro-1,1'-binaphthyl group having a binding arm at the 2,2'-position, wherein the biphenyl group may be substituted by a methyl, methoxy or dialkyl-substituted amino group and the binaphthyl group may be substituted by an alkali sulfonate.

The optionally substituted alkyl groups represented by $R^2$, $R^3$, $R^4$, $R^5$, $R^6$, $R^7$ and $R^8$ in the above formulae mean linear, branched or cyclic alkyl groups optionally having one or more substituents such as halogen atoms and alkoxy groups. Preferable examples thereof include linear or branched alkyl groups having from 1 to 10 carbon atoms and cyclic alkyl groups having from 3 to 8 carbon atoms, more particularly, methyl, ethyl, butyl, octyl and cyclohexyl groups.

The optionally substituted aralkyl groups represented by $R^2$, $R^3$, $R^4$, $R^5$, $R^6$, $R^7$ and $R^8$ in the above formulae mean alkyl groups substituted by an aryl group optionally having one or more substituents such as halogen atoms, alkyl groups and alkoxy groups. Preferable examples of the aryl group therein include optionally substituted phenyl and naphthyl groups. Preferable examples of the alkyl group in the aralkyl groups include those having 1 to 4 carbon atoms, more particularly, benzyl, phenethyl and naphthylmethyl groups.

The optionally substituted aryl groups represented by $R^2$, $R^3$, $R^4$, $R^5$, $R^6$, $R^7$ and $R^8$ in the above formulae mean aryl groups optionally having one or more substituents such as halogen atoms, alkyl groups and alkoxy groups. Preferable examples thereof include unsubstituted phenyl and naphthyl groups and phenyl and naphthyl groups substituted by a chlorine atom, a bromine atom, an iodine atom, a fluorine atom, linear or branched alkyl groups having from 1 to 4 carbon atoms or linear or branched alkoxy groups having from 1 to 4 carbon atoms. More preferable examples thereof include phenyl, naphthyl, p-chlorophenyl, p-bromophenyl, p-fluorophenyl, p-tolyl, p-t-butylphenyl, 3,5-dimethylphenyl and p-methoxyphenyl groups. Among all, phenyl and p-tolyl groups are particularly preferable therefor.

The optionally substituted alkylene groups represented by $A^1$ and $A^2$ mean linear or branched alkylene groups optionally having one or more substituents such as halogen atoms and alkoxy groups. Preferable examples thereof include unsubstituted, linear or branched alkylene groups having from 1 to 5 carbon atoms. Still preferable examples of $A^1$ include ethylene [—(CH$_2$)$_2$—] propylene [—(CH$_2$)$_3$—], butylene [—(CH$_2$)$_4$—] and dimethylethylene [—CH(CH$_3$)CH(CH$_3$)—] groups, while a methylene group (—CH$_2$—) is preferable as $A^2$.

Preferable examples of the ligand represented by the above formula (IV) include trimethylphosphine, triethylphosphine, tributylphosphine, trioctylphosphine, tricyclohexylphosphine, tribenzylphosphine, triphenylphosphine, tri(p-chlorophenyl)phosphine, tri(p-bromophenyl)phosphine, tri(p-fluorophenyl)phosphine, tri(p-tolyl)phosphine, tri(p-t-butylphenyl)phosphine, tri(3,5-dimethylphenyl)phosphine, tri(p-methoxyphenyl)phosphine, methyldiphenylphosphine and dimethylphenylphosphine.

Among the ligands represented by the above formula (V), preferable examples of those wherein $A^1$ is an optionally substituted alkylene group include 1,2-bis(dimethylphosphino)ethane, 1,3-bis(dimethylphosphino)propane, 1,4-bis(dimethylphosphino)butane, 1,2-bis(diphenylphosphino)ethane, 1,3-bis(diphenylphosphino)propane, 1,4-bis(diphenylphosphino)butane, 1,2-bis[di(p-tolyl)phosphino]ethane, 1,3-bis[di(p-tolyl)phosphino]propane, 1,4-bis[di(p-tolyl)phosphino]butane and 2,3-bis(diphenylphosphino)butane (hereinafter referred to as "CHIRAPHOS").

Among the ligands represented by the above formula (V), preferable examples of those wherein $A^1$ is represented by "—$A^2$—Ar—Ar—$A^2$—" include 2,2'-bis(diphenylphosphinomethyl)-1,1'-biphenyl and 2,2'-bis(diphenylphosphinomethyl)-1,1'-binaphthyl.

Among the ligands represented by the above formula (V), preferable examples of those wherein $A^1$ is represented by "—Ar—Ar—" include 2,2'-dimethyl-6,6'-bis(dicyclohexylphosphino)-1,1'-biphenyl (hereinafter referred to as "BICHEP"), 2,2'-dimethyl-6,6'-bis(diphenylphosphino)-1,1'-biphenyl (hereinafter referred to as "BIPHEMP"), 2,2'-dimethoxy-6,6'-bis(diphenylphosphino)-1,1'-biphenyl, 2,2',4,4'-tetramethoxy-6,6'-bis(diphenylphosphino)-1,1'-biphenyl, 2,2'-dimethyl-4,4'-bis(dimethylamino)-6,6'-bis(diphenylphosphino)-1,1'-biphenyl, 2,2'-bis(diphenylphosphino)-1,1'-binaphthyl (hereinafter referred to as "BINAP"), 2,2'-bis(di-p-tolylphosphino)-1,1-binaphthyl (hereinafter referred to as "Tol-BINAP"), 2,2'-bis(di-m-tolylphosphino)-1,1,'-binaphthyl (hereinafter referred to as "m-Tol-BINAP"), 2,2'-bis(di-p-t-butylphenylphosphino)-1,1'-binaphthyl (hereinafter referred to as "t-Bu-BINAP"), 2,2'-bis(di-(3,5-dimethylphenyl)phosphino]-1,1'-binaphthyl (hereinafter referred to as "DM-BINAP"), 2,2'-bis(di-p-methoxyphenylphosphino)-1,1'-binaphthyl (hereinafter referred to as "MeO-BINAP"), 2,2'-bis(di-p-chlorophenylphosphino)-1,1'-binaphthyl (hereinafter referred to as "Cl-BINAP"), 2,2'-bis (dicyclopentylphosphino)-1,1'-binaphthyl (hereinafter referred to as "CpBINAP"), 2,2'-bis (dicyclohexylphosphino)-1,1'-binaphthyl (hereinafter referred to as "CyBINAP") and 2,2'-bis(diphenylphosphino)-5,5',6,6',7,7',8,8'-octahydro-1,1'-binaphthyl (hereinafter referred to as "$H_8$-BINAP").

Among the ligands represented by the above formula (V), CHIRAPHOS and those wherein $A^1$ is represented by —$A^2$—Ar—Ar—$A^2$— or —Ar—Ar— have asymmetric structures and occur as (+)-isomers, (−)-isomers or racemic modifications all of which are usable in the present invention. However, it is preferable to use ligands having no asymmetric structure, in particular, those represented by the formula (IV).

Examples of the auxiliary ligand which may be contained in the ruthenium-phosphine complex include 1,5-cyclooctadiene, benzene, p-cymene, acetonitrile, benzonitrile, pyridine, quinoline, isoquinoline, acetic acid and acetylacetonate.

Preferable examples of the ruthenium-phosphine complex are the complexes 1 to 4 represented by the following formulae (III) and (VI) to (VIII).

$$\text{Complex 1: } RuH_a(X^1)_b L_c \qquad (III)$$

wherein $X^1$ represents a halogen atom or a group represented by "$R^1COO$", wherein $R^1$ represents a hydrogen atom, an alkyl group having from 1 to 4 carbon atoms or a halogenated alkyl group having from 1 to 4 carbon atoms; L represents an organic phosphine compound; a and b are each an integer of from 0 to 2, provided that (a+b) is 2; when L is monodentate ligand, c is an integer of from 3 to 4; and when L is bidentate ligand, c is an integer of from 1 to 2.

Preferable examples of $X^1$ in the formula (III) include a chlorine atom, a bromine atom, an iodine atom, HCOO, $CH_3COO$ and $CF_3COO$. Among all, a chlorine atom is preferable therefor. In the above formula (III), there are 3 combinations of a with b, namely, (a=0; b=2), (a=1; b=1) and (a=2; b=0). Among them, the combination of (a=0; b=2) is a preferable one. When $X^1$ is a halogen atom, then it is particularly preferable that c is 3 or 4.

Preferable examples of the complex 1 are as follows.

$RUH_2(PPh_3)_4$,
$RuHCl(PPh_3)_4$,
$RuH(HCOO) (PPh_3)_3$,
$RuH(CH_3COO) (PPh_3)_3$,
$RuCl_2(PPh_3)_3$,
$RuCl_2(PPh_3)_4$,
$RuBr_2(PPh_3)_4$,
$RuI_2(PPh_3)_4$,
$RuCl_2[P(CH3)Ph_2]_4$,
$RuCl_2[P(CH_3)_2Ph]_4$,
$RuCl_2[P(CH_3)_3]_4$,
$RuCl_2[Ph_2P—(CH_2)_2—PPh_2]_2$,
$RuCl_2(CHIRAPHOS)_2$,
$RuCl_2(BINAP)$,
$Ru(CH_3COO)_2(Tol-BINAP)$ and
$Ru(CF_3COO)_2(Tol-BINAP)$.

$$\text{Complex 2: } (RuH_dL_e)(X^2)_f \qquad (VI)$$

wherein $X^2$ represents $ClO_4$, $PF_6$ or $BF_4$; L is as defined above; when L is monodentate ligand, e is 2 and f is 2 when d is 0; and e is 4 and f is 1 when d is 1; and when L is bidentate ligand, e is 1 and f is 2 when d is 0; and e is 2 and f is 1 when d is 1.

Preferable examples of the complex 2 are as follows.

$[Ru(BINAP)](ClO_4)_2$,
$[Ru(m-Tol-BINAP)] (PF_6)_2$,
$[Ru(MeO-BINAP)] (BF_4)_2$,
$[RuH(BIPHEMP)_2]ClO_4$ and
$[RuH(t-Bu-BINAP)_2] PF_6$.

$$\text{Complex 3: } [(RuX^3)(Bz)L_h](X^4)_g \qquad (VII)$$

wherein $X^3$ represents a halogen atom; Bz represents optionally substituted benzene; $X^4$ represents a halogen atom, $ClO_4$, $PF_6$, $BF_4$ or $BPh_4$, wherein Ph represents a phenyl group, the same will apply hereinafter; L is as defined above; when L is monodentate ligand, h is 2 and g is 1 or g may be 3 when $X^3$ and $X^4$ are each an iodine atom; and when L is bidentate ligand, h is 1 and g is 1 or g may be 3 when $X^3$ and $X^4$ are each an iodine atom.

Examples of the halogen atoms represented by $X^3$ and $X^4$ in the above formula (VII) include chlorine, bromine and iodine atoms.

The optionally substituted benzene represented by Bz in the above formula (VII) means a benzene ring optionally having one or more substituents such as alkyl groups, alkoxy groups, alkoxycarbonyl groups and halogen atoms. Preferable examples thereof include unsubstituted benzene and benzene substituted by alkyl groups having from 1 to 4 carbon atoms, alkoxy groups having from 1 to 4 carbon atoms, alkoxycarbonyl groups having from 1 to 4 carbon atoms, a chlorine atom, a bromine atom or an iodine atom. More particularly, citation may be made therefor of benzene, toluene, xylene, trimethylbenzene, hexamethylbenzene, ethylbenzene, t-butylbenzene, p-cymene, cumene, anisole, methyl benzoate, chlrobenzene, etc.

Preferable examples of the complex 3 are as follows.

$[RuCl(benzene)(BINAP)]Cl$,
$[RuI(benzene) (Tol-BINAP)]I$,
$[RuI(p-cymene)(Tol-BINAP)]I$ and
$[RuI(p-cymene)(BINAP)]I_3$.

$$\text{Complex 4: } (Ru_2Cl_4L_w)(T) \qquad (VIII)$$

wherein T represents a tertiary amine; and L is as defined above; when L is monodentate ligand, w is 4; and when L is bidentate ligand, w is 2.

Examples of the tertiary amine represented by T in the above formula (VIII) include triethylamine, tributylamine, ethyldiisopropylamine, 1,8-bis(dimethylamino)naphthalene, dimethylaniline, pyridine and N-methylpyridine. Among all, triethylamine is preferable therefor.

Preferable examples of the complex 4 are as follows wherein Et represents an ethyl group.

[Ru$_2$Cl$_4$(BINAP)$_2$](NEt$_3$) and
[Ru$_2$Cl4(DM-BINAP)$_2$](NEt$_3$).

Among the complexes as described above, the complexes 1 are preferably employed in the present invention from the viewpoint of the reaction selectivity, etc.

It is known that many of the above-mentioned complexes are usable as catalysts in reactions wherein ketones are hydrogenated to thereby give alcohols. However, it has never been known so far that these complexes are usable for stereoselectively hydrogenating 4-t-butylcyclohexanone to thereby give cis-4-t-butylcyclohexanol with a high purity. It is reported, for example, that a mixture of 2-cyclohexenol with cyclohexanol (70:30) can be obtained by hydrogenating 2-cyclohexenone with the use of RuCl$_2$(PPh$_3$)$_3$ as a catalyst [T. Ohkuma et al., J. Am. Chem. Soc., vol. 117, pp. 10417–10418 (1995)]. However, it has never been suggested that when cis- and trans-isomers are formed by the hydrogenation into an alcohol, the cis-isomer can be selectively obtained, as is in the case of the present invention.

The base containing an alkali metal or an alkaline earth metal to be used in the present invention is a compound represented by, for example, the following general formula (IX):

M(R$^9$)      (IX)

wherein M represents an alkali metal or an alkaline earth metal; and R$^9$ represents a hydroxyl group, an alkoxy group having from 1 to 4 carbon atoms or a mercapto group. Preferable examples of the base include KOH, Ca(OH)$_2$, KOCH$_3$, KOC(CH$_3$)$_3$, LiOH, LiOCH$_3$, LiOC(CH$_3$)$_3$ and NaOH. Among all, those containing alkali metals are preferable and KOH and NaOH are particularly preferable therefor.

In the present invention, the above-mentioned base is employed in an amount of from about 0.5 to 100 equivalents, preferably from about 1 to 40 equivalents to the complex.

Examples of the amine to be used in the present invention are primary, secondary or tertiary amines represented by the following general formula (X):

NR$^{10}$R$^{11}$R$^{12}$      (X)

wherein R$^{10}$, R$^{11}$ and R$^{12}$ are the same or different and each represents a hydrogen atom, an optionally substituted alkyl group, an optionally substituted aralkyl group or an optionally substituted aryl group, provided that R$^{10}$, R$^{11}$ and R$^{12}$ do not represent hydrogen atoms at the same time; primary, secondary or tertiary diamines represented by the following general formula (XI):

NR$^{13}$R$^{14}$—Z—NR$^{15}$R$^{16}$      (XI)

wherein R$^{13}$, R$^{14}$, R$^{15}$ and R$^{16}$ are the same or different and each represents a hydrogen atom, an optionally substituted alkyl group, an optionally substituted aralkyl group or an optionally substituted aryl group; and Z represents an optionally substituted, saturated or unsaturated carbon chain having from 1 to 6 carbon atoms or an optionally substituted, saturated or unsaturated carbon ring having from 3 to 6 carbon atoms; and other cyclic amines.

The optionally substituted alkyl groups represented by R$^{10}$, R$^{11}$, R$^{12}$, R$^{13}$, R$^{14}$ R$^{15}$ and R$^{16}$ in the above formulae mean linear, branched or cyclic alkyl groups optionally having one or more substituents such as alkoxy groups. Preferable examples thereof include linear or branched alkyl groups having from 1 to 10 carbon atoms and cyclic alkyl groups having from 5 to 8 carbon atoms.

The optionally substituted aralkyl groups represented by R$^{10}$, R$^{11}$, R$^{12}$, R$^{13}$, R$^{14}$, R$^{15}$ and R$^{16}$ in the above formulae mean alkyl groups substituted by an aryl group optionally having one or more substituents such as alkyl and alkoxy groups. As the aryl group therein, a phenyl group is preferable. As the alkyl group in the aralkyl groups, those having 1 to 4 carbon atoms are preferable. As a particular example thereof, a benzyl group may be cited.

The optionally substituted aryl groups represented by R$^{10}$, R$^{11}$, R$^{12}$, R$^{13}$, R$^{14}$, R$^{15}$ and R$^{16}$ in the above formulae mean aryl groups optionally having one or more substituents such as alkyl and alkoxy groups. Preferable examples thereof include unsubstituted phenyl and naphthyl groups and phenyl or napthyl groups substituted by linear or branched alkyl groups having from 1 to 4 carbon atoms or linear or branched alkoxy groups having from 1 to 4 carbon atoms.

Particular examples of the amine to be used in the present invention include monoamines such as methylamine, ethylamine, propylamine, isopropylamine, butylamine, isobutylamine, t-butylamine, hexylamine, octylamine, dodecylamine, cyclopentylamine, cyclohexylamine, benzylamine, dimethylamine, diethylamine, dipropylamine, diisopropylamine, dibutylamine, diisobutylamine, di-t-butylamine, dihexylamine, dicyclopentylamine, dicyclohexylamine, dibenzylamine, trimethylamine, triethylamine, tripropylamine, ethyldiisopropylamine, tributylamine, trihexylamine, tribenzylamine, benzyldimethylamine, aniline, p-toluidine, N,N-dimethylaniline, diphenylamine, triphenylamine, piperidine, piperazine, morpholine, N-methylpiperidine, N-methyhlpiperazine and N-methyhlmorpholine; diamines such as ethylenediamine, trimethylenediamine, tetramethylenediamine, pentamethylenediamine, hexamethylenediamine, N-methylethylenediamine, N,N'-dimethylethylenediamine, N,N'-dimethylpropylenediamine, N,N'-dimethyltetramethylenediamine, N,N'-diethylethylenediamine, N,N'-diethylpropylenediamine, N,N'-diethyltetramethylenediamine, N,N'-dibenzylethylenediamine, N,N' -dibenzylpropylenediamine, N,N'-dibenzyltetramethylenediamine, N,N'-diphenylethylenediamine, N,N'-diphenylpropylenediamine, N,N'-diphenyltetramethylenediamine, N,N,N'-trimethylethylenediamine, tetramethylethylenediamine, tetramethylpropylenediamine, tetramethyltetramethylenediamine, tetraethylethylenediamine, tetraethylpropylenediamine, tetraethyltetramethylenediamine, tetrabenzylethylenediamine, tetrabenzylpropylenediamine, tetrabenzyltetramethylenediamine, tetraphenylethylenediamine, tetraphenylpropylenediamine, tetraphenyltetramethylenediamine and o-phenylenediamine; and optically active diamines such as optically active 1,2-diphenylethylenediamine, 1,3-diphenylpropylenediamine, 1,4-diphenyltetramethylenediamine, 1,2-diaminopropane, 1,1-diphenyl-1,2-diaminopropane, 1,1-di(p-methoxyphenyl)-1,2-diaminopropane, 2,3-diaminobutane, 2,4-diaminopentane, 2,5-diaminohexane, 1,2-diaminocyclopentane and 1,2-diaminocyclohexane.

Among the amines as cited above, it is preferable in the present invention to use the diamines represented by the formula (XI), still preferably primary diamines wherein R$^{13}$, R$^{14}$, R$^{15}$ and R$^{16}$ in the formula (XI) are each a hydrogen atom and Z is a saturated carbon chain having from 1 to 4 carbon atoms. Particular examples thereof include ethylenediamine, trimethylenediamine and tetramethylenediamine.

In the present invention, the amine is employed in an amount of from about 1 to 8 equivalents, preferably from about 2 to 4 equivalents, to the complex (in the case of a monoamine), or from about 0.5 to 4 equivalents, preferably from about 1 to 4 equivalents, to the complex (in the case of a diamine).

The production process of the present invention is performed by hydrogenating 4-t-butylcyclohexanone with the use of such a ruthenium-phosphine complex as described above as a catalyst in the presence of the above-mentioned base and amine in a hydrogen gas stream atmosphere. It is recommended to use the catalyst at a molar ratio to the reaction substrate (i.e., 4-t-butylcyclohexanone) ranging from about 1/100 to 1/100,000 [substrate/catalyst (S/C) molar ratio=100 to 100,000], preferably from about 1/200 to 1/50,000 (S/C=200 to 50,000). It is preferable to carry out the reaction under stirring. When the catalyst is used in a small amount, in particular, it is preferable to carry out the reaction under mechanically stirring with a mechanical stirrer, etc.

The reaction temperature ranges usually from about −30° to 250° C., preferably from about 15° to 100° C. Although the reaction time varies depending on various factors such as the concentration of the reaction substrate employed, the amount of the catalyst, temperature and hydrogen gas pressure, the reaction is completed within about several minutes to 80 hours. The completion of the reaction can be confirmed by gas chromatography, etc.

The hydrogen gas pressure ranges from about 1 to 200 atm, preferably from about 1 to 100 atm. Hydrogen may be diluted with other gas(es) which are inert in the reaction. For example, hydrogen may be diluted with methane, nitrogen, argon, helium, carbon dioxide or mixtures thereof.

The reaction of the present invention can be performed substantially by using the substrate alone, i.e., without any solvent. Alternatively, an appropriate solvent may be employed therein. The solvent, if employed, may be an arbitrary one without restriction, so long as it exerts no undesirable effect on the reaction. For example, use can be made of a solvent, either alone or as a mixture thereof, selected from among water; hydrocarbons such as hexane, heptane, octane, nonane, decane, benzene, toluene and xylene; ethers such as tetrahydrofuran, dioxane, dimethoxyethane, diisopropyl ether and diethylene glycol dimethyl ether; esters such as ethyl acetate, butyl acetate, ethyl propionate and ethyl acetoacetate; alcohols such as methanol, ethanol, n-propanol and isopropanol; nitrites such as acetonitrile; amides such as N,N-dimethylformamide; sulfones such as sulfolane and dimethyl sulfoxide; and sulfoxides. Among all, it is preferable to use alcohols such as methanol, ethanol and isopropanol therefor and isopropanol is the most desirable one.

In the present invention, the ratio of the solvent, if employed, to the reaction substrate is not particularly restricted. It is preferable to add the solvent in an amount about 0.5 to 100 times by weight as much as the substrate.

After the completion of the reaction, purification is effected by filtration, concentration under reduced pressure, distillation, etc. in accordance with the conventional manner. Thus highly pure cis-4-t-butylcyclohexanol containing at least 95% by weight of the cis-isomer can be obtained. If required, the highly pure cis-4-t-butylcyclohexanol thus obtained may be distillated or recrystallized from pentane, hexane, etc. and then acetylated by reacting with acetic anhydride in, for example, toluene in the presence of sodium acetate. Thus cis-4-t-butylcyclohexyl acetate, which is useful as a perfume ingredient, having a high purity can be easily produced. Compared with the conventionally marketed 4-t-butylcyclohexyl acetate containing only a small amount of the cis-isomer, the product thus obtained has a gorgeous and intense floral fragrance and, therefore, is useful as a perfume ingredient.

To further illustrate the present invention in greater detail, and not by way of limitation, the following Examples will be given. In these Examples, analytical data were obtained by using the instruments and conditions as will be specified below.

Gas chromatography:

instrument: HP-5890 (manufactured by Hewlett-Packard, Co.)

column: HP-20M fused silica capillary column (0.20 mm×25 m) (manufactured by Hewlett-Packard, Co.)

measuring temperature: 55°–215° C. (program rate 4° C./min)

injection temperature: 250° C.

carrier gas: helium (0.6 ml/min)

Gas chromatography (mass spectrometry):

instrument: M-2000A (manufactured by Hitachi, Ltd.) and HP-5890 Series II (manufactured by Hewlett-Packard, Co.)

column: BC-WAX (0.25 mm×50 m, 0.15 $\mu$m) (manufactured by GL Sciences Inc.)

Infrared spectrometry (IR):

instrument: IR-810 (manufactured by JASCO Corporation)

Proton magnetic resonance spectrometry ($^1$H-NMR):

instrument: Model AMX-400 (400 MHz), FT-NMR analyzer (manufactured by Bruker JAPAN Co., LTD.)

internal standard: tetramethylsilane.

$^{13}$C magnetic resonance spectrometry ($^{13}$C-NMR):

instrument: Model AMX-400 (100 MHz) (manufactured by Bruker JAPAN Co., LTD.).

EXAMPLE 1

Into a stainless autoclave (100 ml) were fed, under a nitrogen atmosphere, 4.0 g (0.026 mol) of 4-t-butylcyclohexanone, 12.5 mg (0.013 mmol) of RuCl$_2$(PPh$_3$)$_3$, 1.04 ml (0.104 mmol) of a 0.1M solution of KOH in isopropanol, 2.89 ml (0.052 mmol) of a 0.018M solution of trimethylenediamine in isopropanol and 10 ml of isopropanol. The mixture was stirred under a hydrogen gas pressure of 50 atm at room temperature for 16 hours. When the reaction mixture was analyzed by gas chromatography, it was found out that 4-t-butylcyclohexanol (weight ratio of cis-isomer:trans-isomer=95: 5) was thus formed at a conversion ratio of 100%. The reaction mixture was filtered under reduced pressure and the oily substance thus obtained was distilled at 113°–115° C./15 mmHg. Thus 3.44 g of the target cis-4-t-butylcyclohexanol with a high purity was obtained (yield: 85%). The physical data of this product are as follows. MS(EI)(m/z): 57 (100), 67 (43), 82 (39), 99 (20), 123 (12). IR (KBr) (cm$^{-1}$): 3300, 2950, 1480, 1440, 1360, 1340, 1030, 1010.

$^1$H-NMR (CDCl$_3$) δ ppm: 4.03 (1H, m), 1.85–1.81 (2H, m), 1.56–1.34 (7H, m), 1.00 (1H, m), 0.86 (9H, s).

$^{13}$C-NMR (CDCl$_3$) δ ppm: 65.8, 48.0, 33.3, 32.5, 27.4, 20.8.

EXAMPLES 2 to 10

By using RuCl$_2$(PPh$_3$)$_3$ as the catalyst, the hydrogenation reaction was performed at room temperature in the same manner as the one described in Example 1 but varying the amount of the catalyst, the type and amount of the base, the amount of trimethylenediamine and the reaction time. Table 1 summarizes the results.

TABLE 1

| Ex. No. | S/C[*1] | Base | Equivalent of base[*2] | Equivalent of $NH_2(CH_3)_3NH_2$[*3] | Time (h) | Conversion rate (%) | Weight ratio cis:trans |
|---|---|---|---|---|---|---|---|
| 2 | 200 | KOH | 1 | 1 | 5 | 100 | 95:5 |
| 3 | 200 | KOH | 1 | 2 | 5 | 100 | 95:5 |
| 4 | 200 | KOH | 4 | 2 | 5 | 100 | 95:5 |
| 5 | 200 | NaOH | 4 | 2 | 5 | 100 | 95:5 |
| 6 | 500 | KOH | 4 | 2 | 5 | 100 | 95:5 |
| 7 | 1000 | KOH | 2 | 1 | 8 | 85 | 95:5 |
| 8 | 1000 | KOH | 4 | 2 | 8 | 100 | 95:5 |
| 9 | 2000 | KOH | 8 | 4 | 16 | 100 | 95:5 |
| 10 | 3000 | KOH | 8 | 4 | 20 | 100 | 95:5 |

[*1]Molar ratio of 4-t-butylcyclohexanone/catalyst.
[*2]Mole number of KOH per mole of the catalyst.
[*3]Mole number of trimethylenediamine per mole of the catalyst.

EXAMPLE 11

By using $RuCl_2(PPh_3)_3$ as the catalyst, the hydrogenation reaction was performed in the same manner as the one described in Example 1 but increasing the amount of the reaction substrate 4-t-butylcyclohexanone. Namely, 30.0 g (0.19 mol) of 4-t-butylcyclohexanone was hydrogenated by using a glass autoclave. Other reaction conditions were as follows. The molar ratio of 4-t-butylcyclohexanone/catalyst (S/C) was 10,000. As the base, KOH was employed in an amount of 2.2 equivalents to the catalyst. As the amine, ethylenediamine was employed in an amount of 1 equivalent to the catalyst. The reaction was performed under a hydrogen gas pressure of 4 atm at 28° C. for 80 hours.

As a result, 29.2 g of 4-t-butylcyclohexanol (cis:trans= 98.3:1.7) was obtained at a conversion ratio of 99.8% (yield: 96%, distilled at 112°–115° C./19 mmHg).

According to the present invention, cis-4-t-butylcyclohexanol, which is useful as a perfume ingredient, can be produced at a high purity. Moreover, the catalyst employed therein is less expensive and required only in a small amount, which makes the process suitable for industrial production and highly advantageous from an economical viewpoint.

While the invention has been described in detail and with reference to specific embodiment thereof, it will be apparent to one skilled in the art that various changes and modifications can be made therein without departing from the spirit and scope thereof.

What is claimed is:

1. A process for producing cis-4-t-butylcyclohexanol containing at least 95% by weight of the cis-isomer represented by the following formula (II):

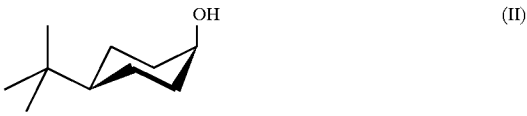

which comprises hydrogenating 4-t-butylcyclohexanone represented by the following formula (I):

in the presence of (1) a catalyst which is a ruthenium-phosphine complex represented by the following formula (III):

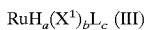

wherein $X^1$ represents a halogen atom or a group represented by $R^1COO$, wherein $R^1$ represents a hydrogen atom, an alkyl group having 1 to 4 carbon atoms or a halogenated alkyl group having from 1 to 4 carbon atoms; L represents an organic phosphine compound; a and b are each an integer of from 0 to 2, provided that (a+b) is 2; when L is a monodentate ligand, c is an integer of from 3 to 4 and where L is a bidentate ligand, c is an integer of from 1 to 2;

(2) an alkali metal base or an alkaline earth metal base; and (3) an alkylenediamine having from 1 to 6 carbon atoms.

* * * * *